(12) United States Patent
Neffgen et al.

(10) Patent No.: US 10,633,491 B2
(45) Date of Patent: Apr. 28, 2020

(54) RADICALLY POLYMERIZABLE COMPOUND

(71) Applicant: Muhlbauer Technology GmbH, Hamburg (DE)

(72) Inventors: Stephan Neffgen, Pinneberg (DE); Olav-Sven Becker, Hamburg (DE)

(73) Assignee: MUHLBAUER TECHNOLOGY GMBH, Hamburg (DE)

( * ) Notice: Subject to any disclaimer, the term of this patent is extended or adjusted under 35 U.S.C. 154(b) by 176 days.

(21) Appl. No.: 15/784,971

(22) Filed: Oct. 16, 2017

(65) Prior Publication Data

US 2018/0105647 A1    Apr. 19, 2018

(30) Foreign Application Priority Data

Oct. 17, 2016    (EP) .................................... 16194165

(51) Int. Cl.
| | | |
|---|---|---|
| C08F 30/02 | (2006.01) | |
| C07F 9/09 | (2006.01) | |
| C08G 73/02 | (2006.01) | |
| C07F 9/38 | (2006.01) | |
| A61K 6/30 | (2020.01) | |
| A61K 6/891 | (2020.01) | |

(52) U.S. Cl.
CPC ............ *C08G 73/0233* (2013.01); *A61K 6/30* (2020.01); *A61K 6/891* (2020.01); *C07F 9/09* (2013.01); *C07F 9/3856* (2013.01); *C07F 9/3873* (2013.01); *C08F 30/02* (2013.01)

(58) Field of Classification Search
None
See application file for complete search history.

(56) References Cited

U.S. PATENT DOCUMENTS

| | | | |
|---|---|---|---|
| 5,376,691 A | 12/1994 | May et al. | |
| 5,501,727 A | 3/1996 | Wang et al. | |
| 6,288,138 B1 | 9/2001 | Takashi et al. | |
| 6,852,775 B1 | 2/2005 | Soglowek et al. | |
| 7,214,276 B2 | 5/2007 | Dahlmann et al. | |
| 7,622,538 B2 | 11/2009 | Moszner et al. | |
| 7,820,733 B2 | 10/2010 | Ohara et al. | |
| 8,183,306 B2 | 5/2012 | Yoshiaki et al. | |
| 8,404,144 B2 * | 3/2013 | Abuelyaman ........ A61K 6/0017 252/79.1 | |
| 8,669,302 B2 | 3/2014 | Blomker et al. | |
| 8,686,061 B2 | 4/2014 | Neffgen et al. | |
| 8,697,772 B2 | 4/2014 | Blomker et al. | |
| 8,883,876 B2 | 11/2014 | Lueck | |
| 8,915,736 B2 | 12/2014 | Blomker et al. | |
| 2003/0134933 A1 | 7/2003 | Jin et al. | |
| 2015/0132544 A1 | 5/2015 | Kano et al. | |
| 2018/0105647 A1* | 4/2018 | Neffgen ................. A61K 6/087 |

FOREIGN PATENT DOCUMENTS

| | | |
|---|---|---|
| DE | 69829259 | 1/2006 |
| DE | 102009005480 | 1/2010 |
| EP | 1194110 | 12/2004 |
| EP | 1444972 | 3/2006 |
| EP | 1872767 | 1/2008 |
| EP | 1878428 | 1/2008 |
| EP | 1674066 | 8/2008 |
| EP | 1878418 | 10/2009 |
| EP | 2110392 | 10/2009 |
| EP | 2371346 | 10/2011 |
| EP | 2450025 | 11/2012 |
| EP | 2198824 | 2/2013 |
| EP | 2512400 | 9/2013 |
| EP | 2662067 | 11/2013 |
| EP | 2436366 | 7/2015 |
| EP | 2436388 | 3/2016 |
| EP | 2436363 | 1/2017 |
| JP | 2006-111584 | 4/2006 |
| JP | 2007-161622 | 6/2007 |
| KR | 20150028464 | 3/2015 |
| WO | WO 01/30306 | 5/2001 |
| WO | WO 03/057792 | 7/2003 |
| WO | WO 2005035590 | 4/2005 |
| WO | WO 2008134024 | 11/2008 |
| WO | WO 2013023138 | 2/2013 |
| WO | WO 2015124559 | 8/2015 |

OTHER PUBLICATIONS

Structure Search—15784971-603090—EICsearch (Year: 2019).*
Bredereck et al., About CH-active Polymerization initiatiors—XIIIth communication Polymerizations and Polymerization Initiators. Makromol Chem, 1966;92:70-90.

* cited by examiner

*Primary Examiner* — Peter A Salamon
(74) *Attorney, Agent, or Firm* — Casimir Jones, S.C.; Mary Ann D. Brow

(57) ABSTRACT

The invention provides a radically polymerizable compound wherein an acid group is joined via a spacer group to a polyethyleneimine group. The polyethyleneimine group has at least one radically polymerizable group in the side chain and/or terminally. The invention relates further to a process for preparing such compounds by cationic polymerization of oxazolines, to the use of such compounds as constituents of a dental material, and to a dental material comprising the compounds of the invention.

16 Claims, No Drawings

RADICALLY POLYMERIZABLE COMPOUND

This application claims the benefit of European Application No. 16194165.3, filed Oct. 17, 2016.

The invention relates to radically polymerizable compounds, to processes for preparing them, to the use of the compounds in a dental material, particularly as constituents of an adhesion promoter, and to polymerizable dental materials which comprise these compounds.

There are numerous radically polymerizable compounds known for use as adhesion promoters that on the one hand contain an acid group, such as a 1,1-bisphosphonic acid group, and on the other hand contain a radically polymerizable group, such as a (meth)acrylate group.

EP 1296634 B1 (Erdmann et al.) and U.S. Pat. No. 8,404,144 B2 (Abuelyaman et al.) describe hydrolysis-stable 1,1-bisphosphonic acids for use in dental materials, these acids having linear alkylene groups as spacer groups and having a (meth)acrylamide group adjoining these spacers.

EP 2662067 (Klee et al.) describes linear polyethyleneimine derivatives which have polymerizable groups and/or carboxyl groups exclusively in the side chains. The polyethyleneimine derivatives are particularly suitable for use in resin-reinforced glass ionomer cements.

EP 2489344 A1 (Salz et al.) describe nonpolymerizable, antimicrobial active ingredients for polymerizable dental materials, said ingredients possibly having an anchor group and a spacer, which may be a polyethyleneimine group or an N-alkylated polyethyleneimine group.

The problem addressed by the invention is that of providing compounds of the above-stated kind which, in or as constituents of polymerizable dental materials, have advantageous properties, preferably imparting good adhesion to the tooth substance (dentine and/or enamel).

This problem is solved by a radically polymerizable compound of the formula I:

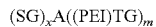

where
$SG=-COOR^1$, $-SO_3R^1$, $-OPO_3R^1{}_2$, or $-PO_3R^1{}_2$;
$R^1$=independently at each occurrence H, $C_1$-$C_7$ alkyl, or monovalent cation, preferably H;
x=1-60, preferably 1-30, preferably 2;
A: hydrocarbon group having 1 to 30 carbon atoms and possibly containing silicon, halogen, nitrogen, phosphorus, oxygen, and sulfur;

$SK=H$, $C_1$-$C_{20}$ alkyl, aryl, alkyl-aryl, $-(CO)NR^3R^4$, $-(CS)NR^3R^4$, $-(CO)OR^3$, $-(CO)R^3$, or $-(SO_2)R^3$;
$R^3$, $R^4$=independently at each occurrence H, alkyl, aryl and/or alkyl-aryl, which may contain halogen, nitrogen, phosphorus, oxygen, and sulfur, or alkenyl;
n=2-100, preferably 3 to 30, more preferably 5 to 15;
$TG=H$, $-NR^6R^7$, $-OR^6$, $-SR^6$, cycloalkenes, $-CR^6R^7R^8$, $-OCOR^9$, or $-NR^6COR^9$, preferably $-NR^6R^7$ or $-OR^6$, more preferably $-OCOR^9$ or $-NR^6COR^9$;
$R^6$, $R^7$, $R^8$=H, $C_1$ to $C_{20}$ alkyl, aryl and/or alkyl-aryl, which may contain halogen, nitrogen, phosphorus, oxygen, and sulfur; a radically polymerizable group which may contain halogen, nitrogen, phosphorus, oxygen, and sulfur, preferably having 1 to 20 carbon atoms; where $R^6$ and $R^7$, with inclusion of the nitrogen atom, may form a ring having 5 to 7 ring atoms and possibly containing heteroatoms;
$R^9$=alkyl, aryl, alkyl-aryl, or alkenyl, preferably having 1 to 19 carbon atoms, more preferably having 1 to 10 carbon atoms;
where PEI or TG comprises at least one radically polymerizable group, with PEI preferably comprising a plurality of radically polymerizable groups;
m=1, 2, or 3, preferably 1 or 2.

The constituents of the stated formula I are briefly elucidated below.

SG is an acid group or ester or salt thereof, preferably an acid group, which possesses the capacity to adhere to a mineral surface. Preferred acid groups are phosphoric acid groups and phosphonic acid groups. Particularly preferred is the phosphonic acid group. SG is preferably bonded exclusively to the spacer group A elucidated in more detail below.

The number x of acid groups bonded to the spacer group A is 1-60, preferably 1-30, more preferably 1 or 2. The acid groups are preferably bonded to directly adjacent carbons, more preferably to the same carbon. An acid group is preferably bonded to a carbon which within the molecule is the furthest away from the polyethyleneimine derivative group or the radically polymerizable group.

A is a spacer group between the acid group SG and the polymerizable groups, or between the acid group and the polyethyleneimine derivative group PEI. The polymerizable groups are constituents of at least one of the two groups PEI (polyethyleneimine derivative group) or TG (terminal and/or organic group) elucidated in more detail below.

With preference, A is an alkylene or aryl-alkylene or alkyl-arylene group, preferably having 1 to 20 carbon atoms, more preferably having 6 to 20 carbon atoms, very preferably a linear $C_2$-$C_{14}$ alkylene group.

PEI is a polyethyleneimine derivative group. The number m of polyethyleneimine derivative groups bonded to the spacer group A is 1 to 3, preferably 1 or 2.

The polyethyleneimine derivative group has a number-average degree of polymerization n of 2 to 100, preferably 3 to 30, more preferably 5 to 15.

The polyethyleneimine derivative group has at least one side chain SK which is not H, preferably a plurality of such side chains SK, more preferably a number of such side chains SK that corresponds to the average degree of polymerization n.

SK is a side chain of the polyethyleneimine derivative group. The at least one side chain preferably has at least one radically polymerizable group; more preferably, a plurality of side chains contain at least one radically polymerizable group.

Where the side chains SK are different groups p, r, etc., they are distributed randomly on the PEI.

Preferred side chains SK comprise, or are selected from, a (CO)N, (CS)N, (CO)O, (CO), or (SO2) group that is bonded directly to a nitrogen atom. Particular preference is given to the (CO) group.

Preferably at least 50%, more preferably at least 80%, more preferably at least 90% of all side chains SK and, with particular preference, all side chains SK contain such a group.

The side chain SK preferably contains no acid group SG.

If the side chain SK and/or $R^6$, $R^7$ is H, alkyl, aryl or alkyl-aryl, the polyethyleneimine unit or TG, respectively, may additionally be in protonated form. The corresponding acid to the counterion of protonated groups preferably has a greater acid strength than the acid group SG; preference is given to the corresponding acid being HCl.

Particularly preferred side chains SK are (meth)acryloyl groups and C5 to C10 alkanoyl groups.

TG is an organic end group or terminal group. The end group TG may have different functional groups according to requirement. The end group TG may contain saturated or unsaturated, open-chain or cyclic hydrocarbon groups, amines, ethers, OH groups, amide groups, or ester groups.

$R^3$ and $R^4$ are preferably selected from the group consisting of $C_1$ to $C_{19}$ alkyl, preferably $C_5$ to $C_{10}$ alkyl, and $C_2$-$C_{19}$ alkenyl, preferably $C_2$ to $C_9$ alkenyl, more preferably —$CR^5CH_2$; where $R^5$=H or $C_1$-$C_7$ alkyl, preferably H or —$CH_3$, more preferably H.

In one particularly preferred embodiment, TG contains an amide group or ester group.

The end group TG preferably is or comprises a radically polymerizable group.

If no side chain SK contains a radically polymerizable group, at least one end group TG must contain at least one polymerizable group. Preferred polymerizable groups are alkenyl groups. Particularly preferred are (meth)acrylamide groups or (meth)acrylate groups. The compound of the invention therefore has at least one polymerizable group at least in one of the two constituents, TG or PEI/SK.

The invention provides radically polymerizable compounds whose physical and chemical properties are readily adaptable to the desired end use through the design of the key constituents SG, A, PEI, and TG. In dental materials, the compounds are able to exhibit and mediate a high adhesive force, and to retain this force durably. The compounds are stable with respect to hydrolysis and therefore have long-term integrity both during storage and after application in the oral environment. With the compounds of the invention, accordingly, it is possible to provide one-part dental materials (single-component systems) for which the user is not required to mix plural components. The dental materials may be given a self-etching and/or self-priming formulation, with no need for pretreatment by etching agents, primers, or adhesion promoters. The compounds of the invention are preferably soluble in the dental material in which they are employed.

One preferred embodiment of the invention possesses the formula II:

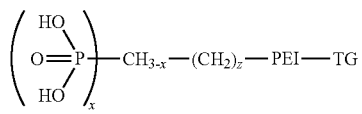

where
x=1 or 2; preferably 2;
z=2 to 14.

Another preferred embodiment of the invention possesses the formula III:

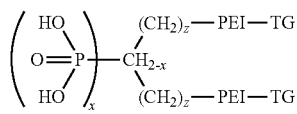

where
x=1 or 2; preferably 2;
z=2 to 14, preferably 2 to 9, or more preferably 2 to 6.

Shown below by way of example are a number of compounds preferred in accordance with the invention:

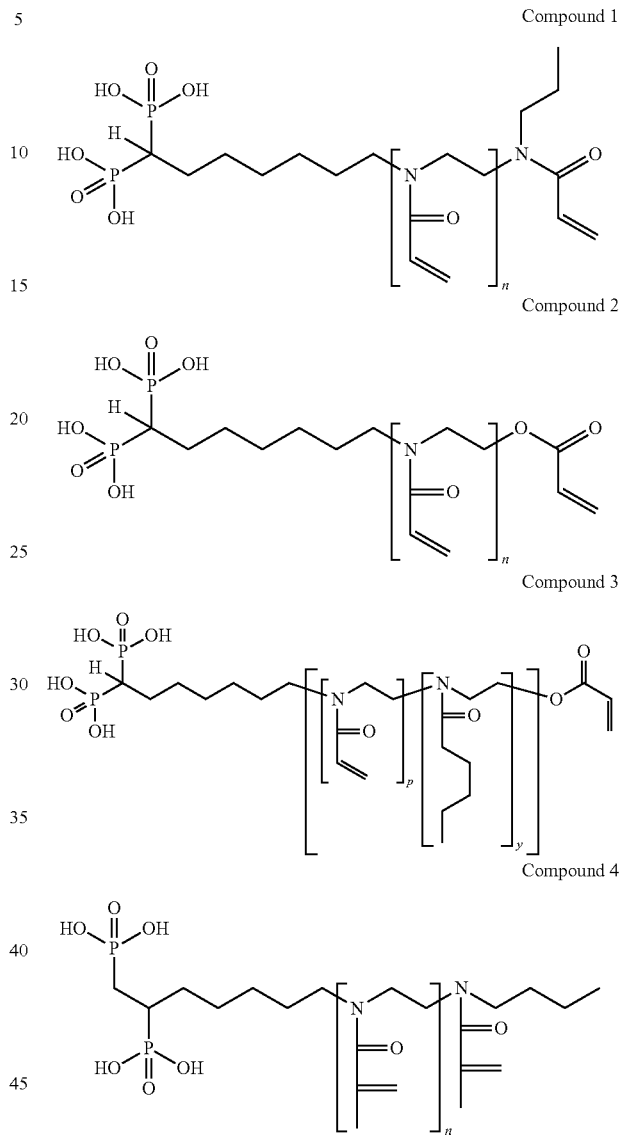

A further subject of the invention is a process for preparing compounds of the invention. In accordance with the process of the invention, the radically polymerizable compound of formula I is synthesized via cationic polymerization of oxazolines.

This is preferably followed by hydrolysis of the resultant polyoxazoline and derivatization of resultant ethyleneimine units.

In a first preferred embodiment, the acid group SG is incorporated via the polymerization initiator of this cationic polymerization. For this purpose, the polymerization initiator has at least one acid derivative group and at least one group which initiates the cationic oxazoline polymerization. The acid derivative group is selected such that it does not initiate or disrupt the oxazoline polymerization, and more particularly the acid derivative group SG here is preferably not a sulfonic acid group or sulfonic acid derivative group.

The initiating groups are electrophilic groups, such as organic halides, especially bromides and iodides, or sulfonic esters, etc. The group initiating the cationic oxazoline polymerization is joined via the spacer group A to the acid group SG. During the initiation and polymerization, the initiating group is replaced by a polyoxazoline group.

Preferred oxazolines are alkyl- and aryloxazolines.

The cationic polymerization of the oxazolines is ended with a termination compound containing a suitable nucleophilic group. Suitable nucleophilic groups are known to the skilled person, examples being primary or secondary amines, hydroxide ions, or carbanions. With the termination compound, the end groups TG or precursors of these groups can be introduced into the radically polymerizable compounds of formula I. The end group TG can be varied in a targeted way with the choice of the termination compound.

Preferred nucleophilic groups of the termination compounds are amine groups and hydroxyl groups.

The resultant polyalkyloxazoline may be subjected to complete or partial hydrolysis to give the polyethyleneimine.

The secondary amino groups of the polyethyleneimine may be derivatized with any compounds which are able to react with secondary amino groups. Preference is given to those which form an amide moiety, examples being acyl chlorides or acid anhydrides. Particularly suitable for the introduction of radically polymerizable groups are (meth)acryloyl chlorides.

In a second preferred embodiment, the end group TG (in analogy to the acid group SG) is incorporated via the polymerization initiator of the cationic polymerization, and the acid group SG (in analogy to the end group TG) is incorporated via the termination compound. The termination compound in that case comprises an acid group SG and the spacer group A.

Suitable nucleophilic groups are amino groups, hydroxyl groups or else carbanions, preferably anions of CH-acidic substances, such as enolates or heteroanalog enolates.

Particularly preferred termination compounds are α-deprotonated tetraalkylesters of methylenebisphosphonic acid, or derivatives of aminoalkylbisphosphonic acids, such as the derivatives of alendronic acid, for example.

Both preferred embodiments are easy to implement, and the properties of the resulting compounds can be adjusted in a targeted way. For example, the hydrophilicity of the compounds can be controlled via the degree of polymerization and/or the nature of derivatization of the polyethyleneimine group and/or the number of side chains in the polyethyleneimine derivative group. This control may be exerted independently of the choice of the acid group SG and/or of the choice of the end group TG. For the introduction of the acid group SG and the end group TG into the resulting compound, moreover, there is a large selection of compounds available.

A further subject of the invention is the use of a compound of the invention as a constituent of or in a dental material, more particularly a radically polymerizable dental material.

In accordance with the invention, radically polymerizable dental materials are to be understood as materials for biomedical use on dental hard substance, especially on enamel and dentine and on bony tissue, especially on the jaw bone.

The radically polymerizable compounds of formula I according to the invention are particularly suitable as adhesion promoters between mineral surfaces and radically polymerizable materials.

Dental materials preferred in accordance with the invention are materials which are used themselves as restorative material, for preparing a restoration, or for joining a restorative material and/or dental restorations made of inorganic materials such as oxide ceramics, silicate ceramics or metals, preferably oxide ceramics, to dental hard substance.

A further subject of the invention is a dental material which comprises:
a) at least one compound of the invention;
b) at least one monomer radically copolymerizable with a);
c) at least one initiator for the radical polymerization;
d) optionally solvents;
e) optionally fillers;
f) customary dental additives.

The material of the invention may be formulated as a single-component system, meaning that there is no need, prior to application, for two or more components of the dental material to be stored separately from one another and mixed with one another.

The dental material of the invention is preferably light-curing, chemically curing or dual-curing.

The dental material of the invention may preferably be employed in one step, meaning that there is no need, prior to application, for any preparatory steps such as etching or priming to be carried out.

The dental material of the invention is therefore preferably self-etching, meaning that there is no need, prior to application, for any conditioning of the dental hard substance that involves an etching step. This means that the bond area of the dental hard substance (especially of the dentine) does not need to be etched with acid in a separate step in order to produce high levels of adhesion.

The dental material of the invention is preferably self-priming, meaning that there is no need, prior to application, to employ any primer or additional adhesion promoter.

In a further variant of the invention, the dental material of the invention may be formulated as a multicomponent system. A subject of the invention in that case is also a two-part or multi-part kit comprising these components for producing a dental material by mixing of these components.

Formulation as a multicomponent system may be preferable especially for chemically curing or dual-curing systems, i.e., if light curing is difficult or impossible. It may also be preferred with the aim of a further improvement in storage stability, since constituents which have little or no compatibility with one another can be separated.

It may be preferable for all radically polymerizable compounds according to formula I in a multi-part (multicomponent) dental material to be contained in a first component of the dental material.

A second component of the dental material preferably contains water or water-rich components and/or radically polymerizable monomers other than compounds of the invention, and/or initiator for the radical polymerization.

Similarly, acid-sensitive compounds and/or compounds which react with the acid group of the radically polymerizable compounds according to formula I to form deleterious products (for example, formation of salts with amines) are preferably contained in a second component of the dental material.

It may be disadvantageous to the shelf life of the materials of the invention if metal compounds, especially heavy metal compounds, are contained in components which at the same time include reducing or oxidizing agents. Unwanted reactions possibly occurring in such cases are known in principle to the skilled person. Examples that may be mentioned include the catalytic decomposition of peroxides by heavy metal compounds, which may also lead to self-hardening of the components in question, or the reduction of heavy metal compounds to elemental metals or less active compounds in lower oxidation states by means of strong reducing agents such as sulfinate salts. A further instance is the known autoxidation reaction of CH-acidic substances in the presence of Cu2+.

In multicomponent materials, therefore, heavy metal compounds are preferably contained in components which do not include any peroxides, any CH-acidic compounds, or else any strong reducing agents that can react with the heavy metal compounds.

Likewise deleterious to the shelf life of the materials of the invention may be reactions of strong nucleophiles, hailing for example from substance group c) (initiator for the radical polymerization), with the electron-deficient double bonds of the constituents from substance groups a) and b). An example would be the reaction of sulfinates with (meth) acrylates or other electrophilic unsaturated groups, leading to the chemical alteration of the formulation.

It is therefore preferred for strong nucleophiles not to be contained together with the constituents from substance groups a) and b) in one component.

In a further preferred embodiment, in which a strong nucleophile can be present in a component together with constituents from substance groups a) or b), the strong nucleophile is not soluble in the liquid mixture in which constituents from substance groups a) or b) are contained.

Preferred constituents b) to f) of a dental material of the invention are disclosed below.

Constituent b)—Monomer Copolymerizable Radically with the Radically Polymerizable Compound of Formula I The dental material of the invention preferably comprises monomers copolymerizable radically with the radically polymerizable compound of formula I.

The radically copolymerizable monomers preferably have at least one acrylate group and/or at least one methacrylate group, more preferably at least two acrylate groups and/or at least two methacrylate groups.

With further preference the dental material of the invention comprises radically copolymerizable monomers which have only one acrylate or methacrylate group and radically polymerizable monomers which have at least two acrylate or methacrylate groups.

Suitable monomers having one acrylate or methacrylate group are, for example, hydroxyethyl (meth)acrylate, hydroxypropyl (meth)acrylate, hydroxybutyl (meth)acrylate, glycerol mono(meth)acrylate, methyl (meth)acrylate, ethyl (meth)acrylate, propyl (meth)acrylate, butyl (meth) acrylate, hexyl (meth)acrylate, octyl (meth)acrylate, lauryl (meth)acrylate, decyl (meth)acrylate, tridecyl (meth)acrylate, 2-ethoxyethyl (meth)acrylate, 2'-ethoxy-2-ethoxyethyl (meth)acrylate, polyethylene glycol mono(meth)acrylate, polypropylene glycol mono(meth)acrylate, polytetramethylene glycol mono(meth)acrylate. Preference is given to hydroxyethyl (meth)acrylate, hydroxypropyl (meth)acrylate, hydroxybutyl (meth) acrylate, glycerol mono(meth) acrylate, and polyethylene glycol mono(meth)acrylate.

Suitable monomers having at least two acrylate or methacrylate groups are, for example, 1,3-propanediol di(meth) acrylate; 1,3-butanediol di(meth)acrylate; 1,4-butanediol di(meth)acrylate; 1,5-pentanediol di(meth)acrylate; neopentyl glycol di(meth)acrylate; 1,6-hexanediol dimethacrylate; 1,9-nonanediol di(meth)acrylate; 1,10-decanediol di(meth) acrylate; 1,12-dodecanediol di(meth)acrylate; glycerol di(meth)acrylate, ethylene glycol di(meth)acrylate; diethylene glycol di(meth)acrylate; triethylene glycol di(meth) acrylate; propoxylated (2) neopentyl glycol di(meth)acrylate; bisphenol A di(meth)acrylate; bisphenol A glycerol di(meth)acrylate (BisGMA); ethoxylated bisphenol A di(meth)acrylate; propoxylated bisphenol A di(meth)acrylate; diurethane di(meth)acrylate (UDMA); tricyclo[5.2.1.0]decane-dimethanol di(meth)acrylates; bis[2-(2-methylacrylamino)ethoxycarbonyl]hexamethylenediamine; trimethylolpropane tri(meth)acrylate; ditrimethylol-propane tetra (meth)acrylate; dipentaerythritol penta(meth)acrylate; dipentaerythritol hexa-(meth)acrylate; and also the polyalicyclic structures described in EP 2436363; EP 2436366; EP 2436388; EP 2450025; U.S. Pat. Nos. 8,697,772; 8,669,302; and WO 2013023138.

Preference is given to bisphenol A di(meth)acrylate; bisphenol A glycerol di(meth)acrylate (BisGMA); ethoxylated bisphenol A di(meth)acrylate; propoxylated bisphenol A di(meth)acrylate; diurethane di(meth)acrylate (UDMA), and tricyclo[5.2.1.0]decane-dimethanol di(meth)acrylates.

The ratio of radically copolymerizable monomers having only one acrylate or methacrylate group to radically copolymerizable monomers having at least two acrylate or methacrylate groups in the dental material is preferably 0:1 to 1:1.

Where it is the case that the (mono(meth)acrylate):higher-functionality (meth)acrylate ratio is >0, the material, from the group of the monomers having one (meth)acrylate group, preferably comprises at least one (meth)acrylate that possesses a substantial water-solubility and is able to function as a phase mediator between highly water-containing regions of the substrates with poorly water-soluble fractions of the substance groups a) and b).

In a further embodiment, the material comprises a substantially water-soluble substance from the group of the higher-functionality methacrylates. Substantially water-soluble substances preferably have a solubility in water at 23° C. of more than 20 g/L.

The dental material of the invention preferably comprises a monomer which is copolymerizable radically with the radically polymerizable compound of formula I and which comprises polyoxyalkylene groups having more than four oxyalkylene units.

The dental material of the invention may comprise further radically polymerizable monomers, oligomers, and prepolymers.

The dental material of the invention preferably contains no monomer which is copolymerizable radically with the radically polymerizable compound of formula I and which comprises a radically polymerizable group other than an acrylate and/or methacrylate group, and more particularly no acrylamide and/or methacrylamide group.

Mixtures of components which comprise acrylate and/or methacrylate groups are notable for a high reactivity for radical polymerizations and also for a broad commercial availability.

The dental material of the invention preferably contains no monomer which is copolymerizable radically with the radically polymerizable compound of formula I and which contains an acid group.

Constituent c)—Initiator for the Radical Polymerization

In one embodiment, the dental material of the invention comprises photoinitiators and/or photoinitiator systems, preferably photoinitiators and/or photoinitiator systems that are suitable for a light wavelength range from 390 nm to 500 nm. These photoinitiators and photoinitiator systems are known to the skilled person.

Preferred photoinitiators and photoinitiator systems are or comprise, respectively, for example, camphorquinone, 1-phenylpropane-1,2-dione, benzil diacetyl, benzil dimethyl ketal, benzil diethyl ketal, benzil di(2-methoxyethyl) ketal, anthraquinone, 1-chloroanthraquinone, 2-chloroanthraquinone, 1,2-benz-anthraquinone, 1-hydroxyanthraquinone, 1-methylanthra-quinone, 2-ethylanthraquinone, 1-bromoanthraquinone, thioxanthone, 2-isopropylthioxanthone, 2-nitrothio-xanthone, 2-methylthioxanthone, 2,4-dimethyl-thioxanthone, 2,4-diethylthioxanthone, 2,4-diisopropyl-thioxanthone, 2-chloro-7-trifluoromethylthioxanthone, thioxanthone 10,10-dioxide, thioxanthone 10-oxide, benzoin methyl ether, benzoin ethyl ether, benzoin isopropyl ether, benzoin isobutyl ether, benzophenone, bis(4-dimethylaminophenyl) ketone, 4,4'-bisdiethyl-aminobenzophenone, acylphosphine oxides such as (2,4,6-trimethylbenzoyl)diphenylphosphine oxide, bis(2,4,6-trimethylbenzoyl) phenylphosphine oxide, benzoyl-trimethylgermanium, dibenzoyldiethylgermanium, and diaryliodonium salts, such as diphenyliodonium hexafluorophosphate, diphenyliodonium hexafluoro-antimonate, bis(4-bromophenyl)iodonium triflate, bis(4-tert-butylphenyl)iodonium hexafluorophosphate, bis(4-fluorophenyl)iodonium triflates, bis(4-methylphenyl)iodonium hexafluorophosphate, (2-bromophenyl) (2,4,6-trimethylphenyl)iodonium triflate, (3-bromophenyl) (2,4,6-trimethylphenyl)iodonium triflate, (2-methylphenyl) (2,4,6-trimethylphenyl)-iodonium triflate, (3-methylphenyl) (2,4,6-trimethylphenyl)iodonium triflate, (4-methylphenyl) (2,4,6-trimethylphenyl)iodonium triflate, (4-nitrophenyl) phenyliodonium triflate, (4-nitrophenyl) (2,4,6-trimethylphenyl)iodonium triflate, phenyl[3-(trifluoromethyl)phenyl] iodonium triflate and/or [3-trifluoromethyl)phenyl] (2,4,6-trimethyl-phenyl)iodonium triflate. Particularly preferred are diphenyliodonium hexafluorophosphate or camphorquinone.

Preferred photoinitiator systems comprise electron donors as coinitiators. Preferred coinitiators are tertiary aromatic or aliphatic amines, as for example N,N-dimethylaminoethyl methacrylate, or aminobenzoates, such as 2-ethylhexyl 4-(dimethylamino)benzoate and ethyl (N,N-dimethylamino) benzoate.

Particularly preferred photoinitiator systems comprise combinations of camphorquinone with at least one dimethylaminobenzoate. Further particularly preferred photoinitiator systems are described in WO 2015124559 A1.

In a further embodiment, the dental material of the invention comprises an activated initiator system for the radical polymerization.

The activated initiator system for the radical polymerization is activatable preferably at room temperature (23° C.) and even more preferably at body temperature (37° C.)

Activated initiator systems consist of at least one activator and at least one initiator.

In order to avoid premature hardening, activator and initiator are contained in separately stored parts of the dental material. The separately stored parts of the dental material are mixed with one another immediately prior to use. In the mixture, a reaction of activator with initiator leads to the initiation of the radical polymerization and hence to the hardening of the dental material.

A preferred activated initiator system is a Redox initiator system.

One preferred Redox initiator system is the amine-peroxide system. The amine-peroxide system comprises at least one amine as reducing agent and at least one peroxide as oxidizing agent. Amine-peroxide systems are known to the skilled person and are described for example in DE 102009005480 (Kohro, Y.), EP 1444972 (Finger, W.), U.S. Pat. No. 7,820,733 (Ohara, Y.), and U.S. Pat. No. 7,214,276 (Qian, X.).

Preferred amines are aliphatic tertiary amines, such as, for example, N,N-dimethylaminoethyl methacrylate, triethylamine, tributylamine, triallylamine, triethanolamine, aromatic secondary and especially aromatic tertiary amines, such as N,N-dimethylaniline, N,N-di(2-hydroxyethyl)-3,5-dimethylaniline, N-methyl-N-(2-methylcarbamoyloxypropyl)-3,5-dimethylaniline, N,N-dimethyl-p-tert-butylaniline, N,N-dimethyl-p-toluidine, N,N-ethyl-p-toluidine, N,N-di(2-hydroxyethyl)-p-toluidine, N,N-di(hydroxymethyl)-p-toluidine, N-methyl-p-toluidine, N,N-dimethyl-sym-xylidine, phenyl-morpholine, methyl 4-dimethylaminobenzoate, ethyl 4-dimethylaminobenzoate, isoamyl 4-dimethylaminobenzoate, and the like. Preference is given to aromatic tertiary amines, such as N,N-dimethyl-p-toluidine, N,N-di(hydroxymethyl)-p-toluidine, N,N-dimethyl-sym-xylidine, and N,N-dimethyl-p-tert-butylaniline.

Preferred peroxides are, for example, dibenzoyl peroxide, 4,4'-dichlorodibenzoyl peroxide, 2,4-dichlorodibenzoyl peroxide, dilauroyl peroxide, tert-butyl peroxide, tert-butyl peroxybenzoate, methyl ethyl ketone peroxide, and tertiary hydroperoxides, such as tert-butyl hydroperoxide, tert-amyl hydroperoxide, p-diisopropylbenzene hydroperoxide, cumene hydroperoxide, pinane hydroperoxide, p-menthane hydroperoxide, and 1,1,3,3-tetramethylbutyl hydroperoxide, 2,5-dimethylhexane-2,5-dihydroperoxide. In certain embodiments it is also possible to use inorganic peroxides, examples being sodium peroxodisulfate, potassium peroxodisulfate, and ammonium peroxodisulfate, as in EP 1 878 428 (Tokui, H.). Particularly preferred are diacyl peroxides, such as dibenzoyl peroxide and dilauroyl peroxide.

Another preferred Redox initiator system comprises at least one substituted thiourea as reducing agent and at least one hydroperoxide as oxidizing agent. Redox initiator systems of this kind are known to the skilled person and are described for example in WO 03057792 (Mitra, S.) and WO 2008134024 (Liu, H.).

Preferred substituted thioureas are benzoylthiourea, 1-(2-pyridyl)-2-thiourea, 1-acetyl-2-thiourea, and 1-(2-tetrahydrofurfuryl)-2-thiourea, or polymerizable thioureas, such as 1-allylthiourea, 1,1-diallylthiourea, 1,3-diallylthiourea, 1-allyl-3-(2-hydroxyethyl)-2-thiourea, (meth)acryloyloxyalkylthiourea, 1-allyl-3-methylthiourea. Particularly preferred are allylthiourea derivatives, 1-(2-pyridyl)-2-thiourea, and 1-(2-tetrahydrofurfuryl)-2-thiourea.

Preferred hydroperoxides are cumene hydroperoxide, tert-butyl hydroperoxide, tert-amyl hydroperoxide, p-diisopropylbenzene hydroperoxide, pinane hydroperoxide, p-menthane hydroperoxide, and 1,1,3,3-tetramethylbutyl hydroperoxide. Particularly preferred are cumene hydroperoxide and tert-amyl hydroperoxide. This system preferably has an acidic promoter, e.g., methacrylic acid, as described in US 2003134933 (Jin, S.).

In a further embodiment, the dental material of the invention comprises an initiator system comprising ascorbic acid or at least one derivative of ascorbic acid as reducing agent and at least one oxidizing agent, as described in U.S. Pat. No. 5,501,727 (Wang, B.) and EP 2371346 (Yarimizu, H.).

Preferred oxidizing agents are selected from the groups of the peroxodisulfates, such as sodium, potassium, ammonium, and alkylammonium peroxodisulfate; the peroxides, such as dibenzoyl peroxide, stearyl peroxide, succinoyl peroxide, and the hydroperoxides, such as cumene hydroperoxide, tert-butyl hydroperoxide, tert-amyl hydroperoxide, and 2,5-dihydroperoxy-2,5-dimethylhexane. Particularly preferred as oxidizing agents are potassium peroxodisulfate, tert-butyl hydroperoxide, and tert-amyl hydroperoxide.

Preferred ascorbic acids and derivatives of ascorbic acid are L(+)-ascorbic acid, dehydroascorbic acid, isoascorbic acid, tolyl-L-ascorbic acid, 2,6-di-o-palmitoyl-L-ascorbic acid, D-araboascorbic acid, L(+)-sodium ascorbate, sodium isoascorbate, and L(+)-calcium ascorbate. Particularly preferred are ammonium, potassium, and sodium isoascorbate.

In a further embodiment, the dental material of the invention comprises the sulfinate-peroxide initiator system, as described in DE 69829259 (Yamamoto, T.), EP 2110392 (Takei, M.), WO 2005035590 (Kalgutar, R.), and EP 1878418 (Tokui, H.).

Preferred sulfinates are aromatic sulfinates, more preferably the alkaline earth metal, alkali metal, and ammonium salts of aromatic sulfinic acids, such as, for example, of benzenesulfinic acid, of p-toluenesulfinic acid, o-toluenesulfinic acid, ethylbenzenesulfinic acid, decylbenzenesulfinic acid, dodecylbenzenesulfinic acid, 2,4,6-trimethylbenzenesulfinic acid, 2,4,6-triisopropylbenzenesulfinic acid, chlorobenzenesulfinic acid, and naphthalenesulfinic acid.

Preferred peroxides are organic peroxides, such as, for example, diacyl peroxides, peroxy esters, dialkyl peroxides, peroxy ketals, ketone peroxides, or hydroperoxides.

Preference is given for example to diacetyldiperoxide, dibenzoyl peroxide, 4,4'-dichlorobenzoyl peroxide, 2,4-dichlorodibenzoyl peroxide, p,p'-dimethoxydibenzoyl peroxide, p,p'-dimethyldibenzoyl peroxide, p,p'-dinitrodibenzoyl peroxide, and m-ditoluoyl peroxide, tert-butylperoxybenzoate, bis-tert-butylperoxyiso-phthalate, 2,5-dimethyl-2,5-bis (benzoylperoxy)hexane, tert-butyl peroxy-2-ethylhexanoate, and tert-butyl peroxyisopropyl carbonate, dicumyl peroxide, dipropyl peroxide, dibutyl peroxide, di-tert-butyl peroxide, dicaprylyl peroxide, and dilauryl peroxide, 1,1-bis(tert-butylperoxy)-3,3,5-trimethylcyclohexane, 1,1-bis (tert-butylperoxy)cyclohexane, and 1,1-bis(tert-hexylperoxy)cyclohexane, methyl ethyl ketone peroxide, cyclohexanone peroxide, and methyl acetoacetate peroxide, cumene hydroperoxide, tert-butyl hydroperoxide, and tert-amyl hydroperoxide, and 2,5-dihydroperoxy-2,5-dimethylhexane.

Preferred peroxides are inorganic peroxides, such as, for example, sodium peroxide, potassium peroxide, aluminum peroxide, ammonium peroxide, ammonium persulfate, and potassium persulfate.

Particularly preferred are dibenzoyl peroxide andسodium or potassium peroxodisulfate.

In a further embodiment, the dental material of the invention comprises as initiator at least one CH-acidic compound, examples being barbituric or thiobarbituric acid derivatives or derivatives thereof, as described for example in H. Bredereck et al., Makromol. Chem. 92, (1966), U.S. Pat. No. 5,376,691 (May, U.), EP 2512400 (Neffgen, St.) or EP 1194110 (Soglowek, W.).

In a further embodiment, the dental material of the invention comprises as initiator at least one salt of a CH-acidic compound, as described for example in EP 1872767 (Lück, R.). In contrast to the CH-acidic compound, the salt of a CH-acidic compound can be stored together with radically polymerizable monomers. Preferred initiator systems which comprise at least one salt of a CH-acidic compound are described in EP 2198824 (Neffgen, St.).

In a further embodiment, the dental material of the invention comprises, as initiator for initiating the radical polymerization, preferably boron compounds, examples being the borates described in JP 2006-111584, which initiate the radical polymerization following chemical activation by acids, or boron compounds as described in EP 1489103 (Tomikawa, T.). Boron compounds of this kind, which initiate in conjunction with atmospheric oxygen, are, for example, trialkylboranes, alkoxyalkylboranes, dialkylboranes, and partially oxidized trialkylboranes. Examples of alkylboranes include triethylborane, tripropylborane, triisopropylborane, tributylborane, tri-sec-butylborane, triisobutylborane, tripentylborane, trihexylborane, trioctylborane, tridecylborane, tricyclopentylborane, or tricyclohexylborane. Preferred alkoxyalkylboranes are butoxydibutylborane, dialkylboranes, 9-borabicyclo[3.3.1]nonane, and partially oxidized boron compounds, such as partially oxidized tributylborane.

It may be preferable for the dental material of the invention to comprise a combination of one or more activated initiator systems with one or more photoinitiator systems. In that case the dental material is dual-curing.

Constituent d)—Solvents

The dental material of the invention preferably comprises at least one solvent, more preferably a mixture of solvents. Preferred solvents are water and organic solvents. Particularly preferred is a mixture of water and organic solvent.

Organic solvents are preferably selected from the group consisting of solvents which are volatile at room temperature (23° C.), having an evaporation number as determined in accordance with DIN 153170 of less than 80. Preferred organic solvents are polar solvents, more preferably polar protic solvents, examples being acetone, the propanols, and the butanols. Particularly preferred is ethanol.

Constituent e)—Fillers

The dental material of the invention preferably comprises fillers.

Preferred fillers are glass powders, glass-ceramic powders, quartz powders, metal oxides, metal hydroxides, spherical fillers as described for example in DE-C 3247800, amorphous cluster fillers such as those described in WO 01/30306, for example, or a mixture of these fillers. Preferred fillers are barium silicate glasses, strontium silicate glasses, borate aluminosilicate glasses, phosphate aluminosilicate glasses, fluoroaluminosilicate glasses, calcium silicates, zirconium silicates, sodium aluminum silicates, phyllosilicates, bentonites, zeolites including the molecular sieves, the oxides and also the hydroxides of the alkali metals and of the alkaline earth metals, and apatites.

Preferred fillers are dental glasses, more preferably dental glasses having an average particle size of between 200 nm and 50 μm.

Preferred fillers are fumed silicas or wet-precipitated silicas.

Preferred fillers are nanofillers having an average particle size <100 nm. Preferred nanofillers are not aggregated and/or not agglomerated.

Preferred fillers have acrylate and/or methacrylate groups on their surface.

Constituent f)—Customary Dental Additives

The dental material of the invention preferably comprises customary dental additives. Preferred additives are inhibitors, stabilizers, accelerators, dyes, fluorinating agents, remineralizing agents, additional x-ray opacifiers, and additional film formers.

The fraction of the radically polymerizable compound of formula I (constituent a)) in the total mass of the dental material of the invention is preferably 1-50 wt %, more preferably 5-50 wt %.

The fraction of radically copolymerizable monomers b) in the total mass of the dental material of the invention is preferably 5-99 wt %, more preferably 5-94 wt %, more preferably 35-94 wt %.

The fraction of the initiator for the radical polymerization c) in the total mass of the dental material of the invention is preferably 0.01-10 wt %, more preferably 0.01-5 wt %.

The fraction of the fillers d) in the total mass of the dental material of the invention is preferably 0-90 wt %. More preferred are lower limits for the filler fraction in the total mass of the dental material of the invention of 0.1 and 1 wt %. Further preferred are upper limits for the filler fraction in the total mass of the dental material of the invention of 80, 65, 45, and 25 wt %.

The solvent fraction e) in the total mass of the dental material of the invention is preferably 0-90 wt %.

Preferred lower limits of the water fraction in the total mass of the dental material of the invention are 0.0, 0.1, 1, and 5 wt %. Preferred upper limits of the water fraction in the total mass of the dental material of the invention are 90, 50, and 15 wt %.

Preferred lower limits of the fraction of organic solvent in the total mass of the dental material of the invention are 0.0, 0.1, 1, and 5 wt %. Preferred upper limits of the fraction of organic solvent in the total mass of the dental material of the invention are 90, 50, and 20 wt %.

The fraction of customary dental additive f) in the total mass of the dental material of the invention is preferably 0.01-10 wt %.

The invention is elucidated below with examples.

PREPARATION EXAMPLES

I) Preparation of Electrophilic Starter Compounds for the Cationic Polymerization of 2-ethyl-2-oxazoline Starter compound A (tetraethyl 11-bromoundecanebisphos-phonate Under nitrogen, 1.4 g of sodium hydride (60% in mineral oil, 35 mmol) was suspended in 15 ml of dry tetrahydrofuran (THF). The suspension was cooled down to 0-5° C. in an ice bath and 8.5 g (30 mmol) of tetraethyl methylenebisphosphonate were added dropwise. 44.4 g (148 mmol) of 1,10-dibromodecane were dissolved in 40 ml of dry THF and added to the reaction mixture. The solution was stirred at RT for 72 h and then admixed with 30 ml of aqueous sodium hydrogencarbonate solution (0.1 mol/l). The THF was then removed on a rotary evaporator and the aqueous phase was extracted by shaking 2× with toluene. The combined organic phases were concentrated on a rotary evaporator. The excess dibromodecane was then removed in a column filtration (SiO2: 1$^{st}$ eluent: heptane/ethyl acetate 1:1, v/v; 2$^{nd}$ eluent: ethanol). The crude product was purified with the aid of flash chromatography (SiO2; ethyl acetate/ethanol, 95:5, v/v). This gave a yellowish oil (yield: 65%).

1H NMR (CDCl3, 300 MHz): δ=1.20-1.38 (m, 10H, CH2), 1.34 (5, 12H, CH3), 1.38-1.48 (m, 2H, CH2), 1.48-1.62 (m, 2H, CH2), 1.72-2.02 (m, 4H, CH2), 2.27 (tt, 1H, CH), 3.41 (t, 2H, CH2Br), 4.03-4.26 (m, 8H, POCH2).

Starter Compound B (tetraethyl 1,13-di-bromotridecane-7,7-bisphosphonate)

Under nitrogen, 1.6 g of sodium hydride (60% in mineral oil, 40 mmol) was suspended in 10 ml of dry tetrahydrofuran (THF). The suspension was cooled down to 0-5° C. in an ice bath and 4.7 g (16 mmol) of tetraethyl methylenebisphosphate were added dropwise. 40 g (164 mmol) of 1,6-dibromohexane were dissolved in 25 ml of dry THF and added to the reaction mixture. The solution was stirred at RT for 72 h and then admixed with 20 ml of aqueous sodium hydrogencarbonate solution (0.1 mol/l). Subsequent treatment took place in analogy to starter compound A. This gave a yellowish oil (yield: 21%).

1H NMR (CDCl3, 300 MHz): δ=1.20-1.38 (m, 4H, CH2), 1.34 (t, 12H, CH3), 1.40-1.62 (m, 8H, CH2), 1.72-2.02 (m, 8H, CH2), 3.41 (t, 4H, CH2Br), 4.03-4.26 (m, 8H, POCH2).

II) Cationic Polymerization of 2-ethyl-2-oxazoline

Under nitrogen, freshly distilled 2-ethyl-2-oxazoline and the respective starter compound, according to table 1, were dissolved in 10 or 15 ml of dry acetonitrile. The solutions were polymerized at 140° C. under pressure in a synthesis microwave (CEM Discovery; microwave power: 100 W) for 10 min.

III) Termination of Cationic Polymerization by Nucleophilic Compounds

III.1) Termination with Amine

After cooling had taken place, n-propylamine was added in a large excess (based on the initiator) to the polymer solution, which was then boiled under nitrogen and under reflux at 70° C. for 24 h. It was subsequently concentrated on a rotary evaporator and the residue was taken up in 10 or 15 ml of dichloromethane. The dichloromethane solution was extracted by shaking first with 10 ml of sodium hydrogencarbonate solution (c(NaHCO3)=1 mol/l, then with 10 ml of water. The organic phase was concentrated on a rotary evaporator and then the residue was again taken up with a little acetonitrile. The solution was subsequently precipitated from cold ether. The precipitation was repeated 2×. The precipitated white solid was dried under a high vacuum.

III.2) Termination with Aqueous Potassium Carbonate Solution

After cooling had taken place, 10 ml of potassium carbonate solution (c=10% by weight) were added to the polymer solution which was then boiled under reflux at 100° C. for 10 h. Subsequent treatment took place in analogy to III.1.

IV) Hydrolysis of poly(2-ethyl-2-oxazoline) to polyethyleneimine

Portions of 4 g of polymer powder were boiled with 100 ml of half-concentrated hydrochloric acid under reflux for 24 h. The hydrochloric acid was then distilled off under reduced pressure and the residue was twice washed with methanol and filtered. The filter residue was dried under a high vacuum. This gave a white solid.

V) Derivatization of Polyethyleneimine

V.1) Derivatization with Acryloyl Chloride

Portions of 1 g of a poly(ethyleneimine)alkanebis-phosphonic acid were admixed with 5 ml of water and adjusted with NaOH solution to a pH of 9. After the solution had cooled to 0-5° C., two-thirds of the amount of acryloyl chloride indicated in table 1 were added over the course of 30 minutes. Thereafter the solution was warmed to RT and stirred for 3 h. The solution was subsequently adjusted to a pH of 11-12, again cooled to 0-5° C., and one-third of the amount of acryloyl chloride indicated in table 1 was added.

After 3 h of stirring at RT, the solution was adjusted to a pH of 1-2 with concentrated hydrochloric acid. The aqueous solution was stabilized with MEHQ, concentrated, and dried under a high vacuum. The residue was taken up with ethanol, the solution was filtered, and the filtrate was concentrated. The solid obtained during concentration was subsequently suspended in diethyl ether, the suspension was filtered, and the residue was dried under a high vacuum. This gave a white solid.

V.2) Derivatization with Acryloyl Chloride and Decanoyl Chloride

Portions of 1 g of a poly(ethyleneimine)alkanebis-phosphonic acid were admixed with 5 ml of water and adjusted with NaOH solution to a pH of 9. After the solution had cooled to 0-5° C., two-thirds of the amount of acryloyl chloride indicated in table 1 were added over the course of 30 minutes. Thereafter the solution was warmed to RT and stirred for 3 h. The solution was subsequently adjusted to a pH of 11-12, again cooled to 0-5° C., and the amount of decanoyl chloride indicated in table 1 was added. After the end of the addition, the solution was warmed to RT and stirred for 3 h. Subsequently, the solution, at a pH of 11-12, was again cooled to 0-5° C. and one-third of the amount of acryloyl chloride indicated in table 1 was added. After 3 h of stirring at RT, the solution was adjusted to a pH of 1-2 with concentrated hydrochloric acid. The aqueous solution was stabilized with MEHQ, concentrated, and dried under a HV. The residue was taken up with ethanol, the solution was filtered, and the filtrate was concentrated. The solid obtained during concentration was subsequently suspended in diethyl ether, the suspension was filtered, and the residue was dried under a high vacuum. This gave a white solid.

The following compounds (for p and r see table 2) were obtained:

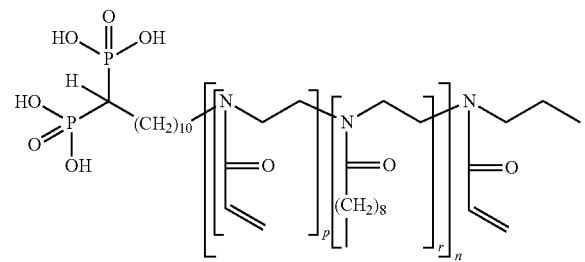

Examples 1, 2, 3

1H NMR (D2O, 300 MHz): δ=0.85-0.95 (3H, CH3), 1.18-1.38 (12H, CH2), 1.45-1.95 (8H, CH2), 2.05-2.35 (1H, CHP), 2.6-4.2 (4H, CONCH2), 5.60-5.95 (1H, CH2CH), 5.95-6.27 (1H, CH2CH), 6.27-6.80 (1H, CH2CH).

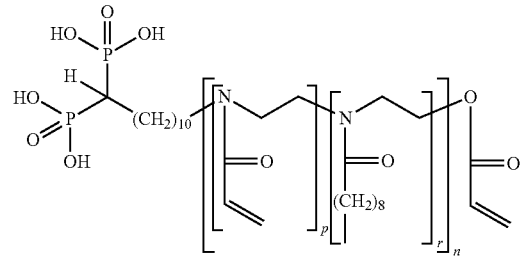

Example 5

1H NMR (D2O, 300 MHz): δ=1.20-1.50 (12H, CH2), 1.50-1.65 (2H, CH2), 1.65-2.00 (4H, CH2), 2.10-2.40 (1H, CHP), 2.6-4.2 (4H, CONCH2), 5.70-6.00 (1H, CH2CH), 6.00-6.35 (1H, CH2CH), 6.35-6.80 (1H, CH2CH).

Example 6

1H NMR (DMSO, 300 MHz): δ=0.86 (3H, CH3), 1.15-1.38 (24H, CH2), 1.38-1.60 (6H, CH2), 1.60-1.80 (2H, CH2), 2.10-2.40 (2H, COCH2), 2.8-4.3 (4H, CONCH2), 5.55-5.80 (1H, CH2CH), 6.0-6.30 (1H, CH2CH), 6.45-6.90 (1H, CH2CH).

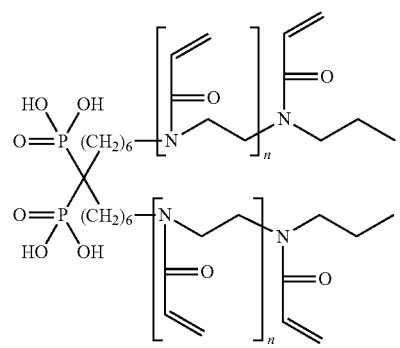

Example 4

1H NMR (D2O, 300 MHz): δ=0.85-0.95 (6H, CH3), 1.1-1.95 (24H, CH2), 2.6-4.2 (8H, CONCH2), 5.6-5.95 (2H, CH2CH), 5.98-6.27 (2H, CH2CH), 6.30-6.80 (2H, CH2CH).

TABLE 1

| Ex. | Starter | Starter [mmol] | Oxazoline [mmol] | Termination Compound | $n_{th}$ | Yield [wt %] | $n_{NMR}$ | Derivatization compound | Derivatization compound [mmol] |
|---|---|---|---|---|---|---|---|---|---|
| 1 | A | 3.9 | 18.5 | n-propyl-amine | 5 | 70 | 5 | acryloyl chloride | 6 |
| 2 | A | 3.9 | 39 | n-propyl-amine | 10 | 70 | 7 | acryloyl chloride | 12 |
| 3 | A | 3.9 | 78 | n-propyl-amine | 20 | 52 | 14 | acryloyl chloride | 24 |

TABLE 1-continued

| Ex. | Starter | Starter [mmol] | Oxazoline [mmol] | Termination Compound | $n_{th}$ | Yield [wt %] | $n_{NMR}$ | Derivatization compound | Derivatization compound [mmol] |
|---|---|---|---|---|---|---|---|---|---|
| 4 | B | 1.2 | 24 | n-propyl-amine | 10 | 37 | 8 | acryloyl chloride | 24 |
| 5 | A | 3.9 | 39 | OH⁻ | 10 | 67 | 10 | acryloyl chloride | 12 |
| 6 | A | 3.9 | 39 | OH⁻ | 10 | 67 | 10 | acryloyl chloride | 6 |
|   |   |   |   |   |   |   |   | decanoyl chloride | 4 |

TABLE 2

| Ex. | SG | x | A | $n_{PEI}$ | SK | p* | r* | TG | m |
|---|---|---|---|---|---|---|---|---|---|
| 1 | —PO(OH)$_2$ | 2 | CH—(CH$_2$)$_{10}$ | 5 | —CO—CH=CH$_2$ | 5 |  | —N (CH$_2$—CH$_2$—CH$_3$)(CO—CH=CH$_2$) | 1 |
| 2 | —PO(OH)$_2$ | 2 | CH—(CH$_2$)$_{10}$ | 10 | —CO—CH=CH$_2$ | 10 |  | —N (CH$_2$—CH$_2$—CH$_3$)(CO—CH=CH$_2$) | 1 |
| 3 | —PO(OH)$_2$ | 2 | CH—(CH$_2$)$_{10}$ | 20 | —CO—CH=CH$_2$ | 20 |  | —N (CH$_2$—CH$_2$—CH$_3$)(CO—CH=CH$_2$) | 1 |
| 4 | —PO(OH)$_2$ | 2 | (CH$_2$)$_6$—C—(CH$_2$)$_6$ | 10 | —CO—CH=CH$_2$ | 10 |  | —N (CH$_2$—CH$_2$—CH$_3$)(CO—CH=CH$_2$) | 2 |
| 5 | —PO(OH)$_2$ | 2 | CH—(CH$_2$)$_{10}$— | 10 | —CO—CH=CH$_2$ | 10 |  | —O—CO—CH=CH$_2$ | 1 |
| 6 | —PO(OH)$_2$ | 2 | CH—(CH$_2$)$_{10}$— | 10 | —CO—CH=CH$_2$/—CO—(CH$_2$)$_8$—CH$_3$ | 5 | 5 | —O—CO—CH=CH$_2$ | 1 |

*n = p + r

In the subsequent examples, dental materials of the invention are produced and their adhesion properties are tested using light-curing dental adhesives. For this purpose the shear bond strength (SBS) on dental enamel was ascertained.

For the production of the light-curing dental adhesives, their individual components were mixed by stirring at room temperature, in the absence of light that initiates photopolymerization, until a homogeneous solution was formed.

In order to determine the shear bond strength (SBS), bovine incisors without pulp were embedded into a cold-polymerizing resin (Viscovoss GTS with MEKP MEH hardener; Voss Chemie). Immediately before use, the embedded teeth were sanded down wet to the enamel (P120 sandpaper) and then reground wet with a fine sandpaper (P500). Prior to being used, the teeth were stored in demineralized water. For measurement, the teeth were taken from the demineralized water and the moisture was removed from the ground surface using oil-free compressed air. The adhesion promoter was applied with a microbrush and rubbed in for 10 s. After an exposure time of 20 s, the solvents were carefully blown away and the surface was exposed for 10 s to a dental lamp (MiniLED, ACTEON Germany, Mettmann, Germany).

Thereafter a two-part Teflon mold with a hole of 3.0 mm in diameter (ISO/TS 11405:2003) was mounted, and was fixed with a metal bracket, and the cavity was filled with a dental composite (Ecusit, DMG, Hamburg, Germany) and exposed for 40 s (MiniLED). After curing had taken place, the Teflon mold was removed and protruding residues of the cured adhesion promoter were removed using a scalpel. The test specimens prepared were stored at 37° C. for 23 h and at 23° C. for 1 h. The test specimens were then subjected to measurement with a shearing apparatus according to ISO10477:2004 and in an apparatus for determining a force-distance diagram (Z010/TN2A, Zwick GmbH & Co., Ulm, Germany) with a rate of advance of 0.5 mm/min. The result is reported in the form of a mean value with standard deviation. The testing was carried out on 10 test specimens in each case.

TABLE 3

Compositions of the light-curing dental adhesives and the shear bond strength (SBS) results

|  | Composition 1 [wt %] | Composition 2 [wt %] |
|---|---|---|
| Ex. 2 | 10.6 | 0 |
| Ex. 5 | 0 | 10.6 |
| BisGMA | 24.8 | 24.8 |
| HEMA | 29.6 | 29.6 |
| Ethanol | 19.8 | 19.8 |
| Water | 13 | 13 |
| CQ | 0.8 | 0.8 |
| EHA | 1.4 | 1.4 |
| BHT | 0.01 | 0.01 |
| SBS [MPa] | 12.1 ± 3.6 | 16.5 ± 6.8 |

BisGMA = bisphenol A diglycidyl dimethacrylate; HEMA = 2-hydroxyethyl methacrylate; CQ = camphorquinone; EHA = 2-ethylhexyl 4-(dimethylamino)benzoate; BHT = 3,5-di-tert-butyl-4-hydroxytoluene

What is claimed is:

1. A radically polymerizable compound of the formula I:

(SG)$_x$A((PEI)TG)$_m$ where

SG=—COOR$^1$, —SO$_3$R$^1$, —OPO$_3$R$^1{}_2$, or —PO$_3$R$^1{}_2$;

R$^1$=independently at each occurrence H, C$_1$-C$_7$ alkyl, or monovalent cation;

x=1-60;

A: hydrocarbon group having 1 to 30 carbon atoms and possibly containing silicon, halogen, nitrogen, phosphorus, oxygen, and sulfur;

SK=H, $C_1$-$C_{20}$ alkyl, aryl, alkyl-aryl, —(CO)NR$^3$R$^4$, —(CS)NR$^3$R$^4$, —(CO)OR$^3$, —(CO)R$^3$, or —(SO$_2$)R$^3$;

R$^3$, R$^4$=independently at each occurrence H, alkyl, aryl and/or alkyl-aryl, which may contain halogen, nitrogen, phosphorus, oxygen, and sulfur, or alkenyl;

n=2-100;

TG=H, —NR$^6$R$^7$, —OR$^6$, —SR$^6$, cycloalkenes, —CR$^6$R$^7$R$^8$, —OCOR$^9$, or —NR$^6$COR$^9$;

R$^6$, R$^7$, R$^8$=H, $C_1$ to $C_{20}$ alkyl, aryl and/or alkyl-aryl, which may contain halogen, nitrogen, phosphorus, oxygen, and sulfur; a radically polymerizable group which may contain halogen, nitrogen, phosphorus, oxygen, and sulfur; where R$^6$ and R$^7$, with inclusion of the nitrogen atom, may form a ring having 5 to 7 ring atoms and possibly containing heteroatoms;

R$^9$=alkyl, aryl, alkyl-aryl, or alkenyl;

where PEI or TG comprises at least one radically polymerizable group;

m=1, 2, or 3.

2. The compound as claimed in claim 1, wherein SG is selected from the group consisting of —OP$_3$R$^1$$_2$ or —PO$_3$R$^1$$_2$.

3. The compound as claimed in claim 1, wherein A is an alkylene or aryl-alkylene or alkyl-arylene group.

4. The compound as claimed in claim 1, wherein at least 50% of SKs are selected from the group consisting of —(SO$_2$)R$^3$ and —(CO)R$^3$.

5. The compound as claimed in claim 1, wherein R$^3$ and R$^4$ are selected from the group consisting of $C_1$ to $C_{19}$ alkyl, and $C_2$-$C_{19}$ alkenyl.

6. The compound as claimed in claim 1, wherein SK has no acid group SG.

7. The compound as claimed in claim 3 of the formula II:

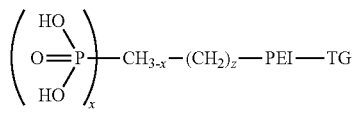

where
x=1 or 2;
z=2 to 14.

8. The compound as claimed in claim 3 of the formula III:

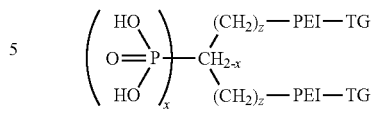

where
x=1 or 2;
z=2 to 14.

9. A process for preparing a compound as claimed in claim 1, which comprises cationic polymerization of oxazolines.

10. The process as claimed in claim 9, wherein the cationic polymerization is followed by hydrolysis of the resultant polyoxazoline.

11. The process as claimed in claim 9, wherein the acid group SG is incorporated via the polymerization initiator of the cationic polymerization; and wherein the end group(s) TG is/are incorporated via the termination compound of the cationic polymerization.

12. The process as claimed in claim 9, wherein the end group(s) TG is/are incorporated via the polymerization initiator of the cationic polymerization; and wherein the acid group SG is incorporated via the termination compound of the cationic polymerization.

13. A radically polymerizable dental material comprising as a constituent a compound as claimed in claim 1.

14. A dental material which comprises:
a) at least one compound as claimed in claim 1;
b) at least one monomer radically copolymerizable with a);
c) at least one initiator for the radical polymerization;
d) optionally solvents;
e) optionally fillers;
f) customary dental additives.

15. The dental material as claimed in claim 14, wherein the fraction of the components as a proportion of the total mass is as follows:
component a): 1-50 wt %;
component b): 5-99 wt %;
component c): 0.01-10 wt %;
component d): at least 0.1 wt %; not more than 80 wt %;
component e): 0-90 wt %.

16. A method of promoting adhesion between a mineral surface and radically polymerizable materials comprising applying a compound as claimed in claim 1 to a mineral surface as an adhesion promoter.

* * * * *